United States Patent [19]

Steffan et al.

[11] Patent Number: 5,814,514
[45] Date of Patent: Sep. 29, 1998

[54] BIODEGRADATION OF THE GASOLINE OXYGENATES

[75] Inventors: Robert Jon Steffan, Newtown; Charles Whitman Condee, Morrisville; Kevin Rock McClay, Morrisville; Jennifer Diane Michelson, Yardley, all of Pa.; Mary F. DeFlaun, Mercerville, N.J.

[73] Assignee: Envirogen, Inc., Lawrenceville, N.J.

[21] Appl. No.: 677,516

[22] Filed: Jul. 10, 1996

[51] Int. Cl.$^6$ .................................................. C07C 00/00
[52] U.S. Cl. ..................... 435/262; 435/262.5; 435/863
[58] Field of Search ............................... 435/262, 262.5, 435/264, 281, 283

[56] References Cited

U.S. PATENT DOCUMENTS

| 5,399,495 | 3/1995 | Patt et al. ............................. | 435/254.1 |
| 5,427,944 | 6/1995 | Lee et al. .............................. | 435/262.5 |
| 5,474,934 | 12/1995 | Adamus et al. ...................... | 435/262.5 |

OTHER PUBLICATIONS

Vanderberg et al., Dehalogenation by Mycobacterium vaccae JOB–5, Canadian Journal of Microbiology, Mar. 1994, vol. 40, No. 3, pp. 169–172.
M.S. Reisch, *Chemical & Engineering News,* Apr. 11, 1994; pp. 12–15.
Trenton Times, Nov. 13, 1994.
Anderson, "Health Studies Indicate MTBE is Safe Gasoline Additive," *Chemical and Engineering News,* 9–18, Sep. 20, 1993.
Robinson, M., R.H. Bruner, and G.R. Olson, "Fourteen and ninety day oral toxicity studies of methyl tertiary butyl ether in Sprague–Dawley rats," *J. Am. Coll. Toxicol.,* 9:525–540 (1990).
American Petroleum Institute, Chemical Fate and Impact of Oxygenates in Groundwater: Solubility of BTEX from Gasoline–Oxygenate Mixtures, Pub. No. 4531, 1991.
Yeh, C. and Noval, J., "Anaerobic biodegradation of gasoline oxygenates in soils," *Water Environment Research,* 66(5), 744–752 (1994).
Yeh, C. and Novak, J., "The effect of hydrogen peroxide on the degradation of methyl and ethyl tert–butyl ether in soils," *Water environment Research,* 67(5), 828–834 (1995).
Brockman, F.J., W. Payne, D.J. Workman, a. Soong, S. Manley, and T.C. Hazen, "Effect of gaseous nitrogen and phosphorous injection on in situ bioremediation of a trichloroethylene–contaminated site," *J. Haz. Material,* 41:287–298 (1995).
Marley, M.D., D.J. Hazebrook, and M.T. Walsh, "The application of in situ air sparging as an innovative soils and groundwater remediation technology," *Groundwater Monitoring Review,* 2:137–145 (1992).
Lombard, K.H., J.W. Borthen and T.C. Hazen, 1994, The design and management of system components for in situ methanotrophic bioremeidation of chlorinated hydrocarbons at the Savannah River Site, in: R.E. Hinchee (ed.), *Air Sparging for Site Remediation,* Lewis Publishers, Boca Raton, FL, pp. 81–96.

Hazen, T.C. et al., 1994, Summary of in situ bioremediation demonstration (methane biostimulation) via horizontal wells at the Savannah River Site Integrated Demonstration Project, in : *In Situ Remediation: Scientific Basis for Current and Future Technologies,* Battelle Press, Richland, WA, pp. 137–150.
"Removing Gasoline from Soil and Groundwater Through Air Sparging," by Michael C. Marley, *Remediation,* 121–131, Spring 1992.
Roberts, P.V., G.D. Hopkins, D.M. Mackay, and L. Semprini, "A field evaluation of in situ biodegradation of chlorinated ethanes: Part I, methodology and field site characterization," *Ground Water,* 28:591–604 (1990).
Marley, M.C., E.X. Droste, H.H. Hopkins, and C.J. Bruell, "Use Air Sparging to Remediate," *Environ. Engineer. World,* 6–14 (Mar.–Apr. 1996).
Semprini, L. and P.L. McCarty, "Comparison between model simulations and field results from in situ biorestoration of chlorinated aliphatics: Part 1, biostimulation of methanotropic bacteria," *Ground Water,* 29:365–374 (1991).
Perry, Substrate Specificity in Hydrocarbon Utilizing Microorganisms, *Antonie van Leeuwenhoek,* 27–36 (1968).
L. P. Wackett et al., *Applied and Environmental Microbiology* 55:2960–2964 (1989).
Hareland, W., R. L. Crawford, P. J. Chapman, and S. Dalgey. 1975. Metabolic function and properties of 4–hydroxyphenylacetic acid 1–hydroxylase from *Pseudomonas acidovorans. J. Bacteriol.* 121:272–285.
Speitel, G.E., R.C. Thompson, and D. Wiessman, "Biodegradation kinetics of *Methylosinus trichosporium* OB3b at low concentrations of chloroform in the presence and absence of enzyme competition of methane," *Water Res.,* 27:15–24 (1993).
Salanitro et al., "Isolation of a Bacterial Culture that Degrades Methyl t–Butyl Ether," *Applied and Environmental Microbiology,* 2593–2596 (Jul. 1994).
Burback, B.L. and Perry, J.J., *Applied and Environmental Microbiology,* 59(4), 1025–1029 (1993).
Vanderberg et al., Abstract Q–111, "Catabolism of Recalcitrant Compounds by Combined Cultures of Soild Mycobacteria," from 94th General Meeting of the Am. Soc. Microbiol., Las Vegas (1994).
Mo et al. 1995; Abstracts Ann. Meet. Am. Soc. Microbiol., Q51.
Mormile et al. "Anearobic Biodegradation of Gasoline Oxygenates: Extrapolation of Information to Multiple Sites and Redox Conditions," *Environ. Sci. Technol.,* 28:1727–1732, 1994.

*Primary Examiner*—David A. Redding
*Attorney, Agent, or Firm*—Synnestvedt & Lechner

[57] ABSTRACT

The present invention is directed to a method for degrading an undesirable ether-based environmental contaminant by contacting the ether with a propane-oxidizing microorganism or with an isopropanol-oxidizing microorganism to convert the ether to innocuous compounds which are environmentally acceptable, including treating the ether-based contaminants in situ or removing them from the contaminated site for treatment in a bioreactor. Examples of ether-based compounds which can be degraded are tertiary butyl ethers of the type utilized as gasoline oxygenates, for example, methyl tert-butyl ether, ethyl tert-butyl ether, and methyl tert-amyl ether and also ether solvents, for example, tetrahydrofuran.

22 Claims, 7 Drawing Sheets

BIODEGRADATION OF THE GASOLINE OXYGENATES

FIELD OF THE INVENTION

This invention relates to a method for converting undesirable environmental contaminants into environmentally acceptable materials. More particularly, the present invention relates to a biological method for converting organic compounds which are water and soil contaminants into innocuous compounds.

The field of the present invention will be described initially in connection with the contaminant methyl-tert-butyl ether (hereafter also referred to as "MTBE"). It should be understood that the present invention has applicability to the treatment of other "ether" contaminants, as will be described below.

MTBE has been used in "premium" gasoline since 1979 as a high octane additive which functions as an oxygenate. Its use has replaced lead and other additives such as benzene, toluene, ethylbenzene and xylenes, which are often referred to as "BTEX" and which are considered highly contaminating materials. More recently, for areas of the country with relatively high air pollution, the 1990 Clean Air Act requires that oxygenates be used in all grades of gasoline to reduce vehicle emissions which constitute air toxics, for example, carbon monoxide and volatile organic compounds (VOCs). Oxygenates cause fuel to burn more cleanly, reducing the amounts of ozone, carbon monoxide, toxics and other pollutants present in vehicle emissions. The current goal of gasoline reformulation is to reduce gasoline's benzene content by 33% and other contaminating organics by at least 15%.

MTBE is the most widely used oxygenate in the United States. In 1992, more than 1.8 billion gallons of MTBE was used in gasoline. Its use has continued to increase each year since 1992 (Anderson, "Health Studies Indicate MTBE is a Safe Gasoline Additive," *Chemical and Engineering News*, Sep. 20, 1993). MTBE producers have invested billions of dollars into plants already in operation or planned. More than 29 companies now produce MTBE in the U.S. And in 1993, production of MTBE exceeded 24 billion gallons, making it second on the list of organic chemicals produced in the U.S. (M.S. Reisch, *Chemical & Engineering News*, Apr. 11, 1994; p. 2–15).

The toxicity of MTBE is still in question. A recent Italian study suggested that MTBE poses a significant cancer risk (Trenton Times, Nov. 13, 1994). Other studies have suggested that MTBE is not very toxic to humans (Anderson, "Health Studies Indicate MTBE is Safe Gasoline Additive," *Chemical and Engineering News*, 9–18, Sep. 20, 1993).

Without regard to whether MTBE is or is not toxic, it is a fact that as an ether, it has relatively low odor and taste thresholds compared to other organic compounds. MTBE's odor threshold in water is about 45 to about 95 ppb. Its taste threshold in water is about 134 ppb (American Petroleum Institute 1993). This means that MTBE can be detected in drinking water through odor and taste at relatively low concentrations. The Maximum Drinking Water Levels for MTBE are between 540 and 700 ppb (Gilbert and Calabrese, "Developing a Standard for MTBE in Drinking Water," *Regulating Drinking Water Quality*, 231–252). Based on rat model studies, the no-observable-adverse-effect-level (NOAEL) is 100 mg/kg/day (Robinson, M., R. H. Bruner, and G. R. Olson, "Fourteen and ninety day oral toxicity studies of methyl tertiary butyl ether in Sprague-Dawley rats," *J. Am. Coll. Toxicol.*, 9:525–540 (1990)).

The greatest human exposure routes of MTBE are through drinking contaminated water, use of the water in cooking, and inhalation during bathing.

The chances of such exposure are not insignificant since vast amounts of MTBE-containing gasoline are stored in underground storage tanks, including tanks which leak. Seepage of MTBE from leaky tanks into groundwater and spillage of MTBE during tank filling operations and transfer operations at distribution terminals have led to considerable contamination of groundwater near these tanks. Because MTBE is highly soluble in water (43,000 ppm), it is now often found as plumes in groundwater near service stations, related storage facilities and filling terminals throughout the United States (American Petroleum Institute, Chemical Fate and Impact of Oxygenates in Groundwater: Solubility of BTEX from Gasoline-Oxygenate Mixtures," Pub. No. 4531, 1991). A market survey by The Jennings Group (1993) estimated that there are greater than 234,000 federally regulated contaminated underground storage tank (UST) sites in the United States and greater than 42,000 hazardous sites.

The recalcitrance of MTBE relative to other gasoline components makes it particularly resistant to inexpensive biological treatment approaches such as bioventing or biosparging. Conversion or "remediation" of the contaminated media to innocuous, environmentally-acceptable compounds, therefore, has been particularly difficult. Furthermore, MTBE can be difficult to air strip from ground water and trap on activated carbon, thereby limiting air sparging/soil vapor extraction (AS/SVE) approaches to remediation. In a recent study of 15 sites, stripping efficiencies of as low as 56% were observed (American Petroleum Institute, supra). And yet this method has been deemed to be the most effective method for remediating contaminated groundwater.

There are other ether-based compounds that are also widely used and that are considered contaminants. Examples of such ether-based compounds include cycloaliphatic compounds, for example, tetrahydrofuran, a widely used solvent. Examples of other aliphatic ethers which are considered contaminants are ethyl-tert-butyl ether ("ETBE"), tert-amyl methyl ether ("TAME") and diisopropyl ether ("DIPE"), which are used as gasoline oxygenates.

As production of such ether-based compounds continues to grow, it can be expected that the incidence and severity of spills will increase and that the threat to the water supply will become more severe. The present invention is related to the biological treatment of ether compounds to counter such a threat by providing means to efficiently remediate contaminated sites.

REPORTED DEVELOPMENTS

It appears that relatively little work has been done to develop means for biodegrading ethers of the aforementioned type. In one study, an aerobic consortia isolated from acclimated sludge was maintained on MTBE which served as the sole source of carbon for the consortia (Salanitro et al., "Isolation of a Bacterial Culture that Degrades Methyl t-Butyl Ether," *Applied and Environmental Microbiology*, July 1994). MTBE was degraded to tertiary-butyl alcohol ("TBA") which was also degraded by the enrichment culture. The consortia is described as comprising at least 6 different uncharacterized bacteria. The physiology of the individual organisms is not reported. It is reported that the consortia appear to have a significant population of nitrifying bacteria.

Another recent study reported on the isolation from soil and sludge of several aerobic organisms that were able to degrade MTBE (Mo et al. 1995; Abstracts Ann. Meet. Am. Soc. Microbiol., Q51), but the degradation was relatively slow and inefficient, and the characteristics of the degradative organisms were not reported.

It appears that in situ degradation of MTBE in aquifers also has not been studied extensively. However, recent unpublished studies by researchers at Mobile Oil Corporation have provided evidence, based on historical concentrations of MTBE in groundwater, that natural attenuation of MTBE may occur over very long periods of time in aquifers. Apparent degradation occurs after the concentrations of benzene, toluene, ethylbenzene or xylene (BTEX) are reduced to low levels. The identity of the organisms responsible for the decline in MTBE were not reported. In further studies, it was observed that MTBE was partially transformed in only one of several anaerobic sediment samples tested (Mormile et al. "Anaerobic Biodegradation of Gasoline Oxygenates: Extrapolation of Information to Multiple Sites and Redox Conditions," *Environ. Sci. Technol.*, 28:1727–1732, 1994). Transformation of MTBE in the one active sample required more than 152 days of incubation, resulted in only about 50% transformation of MTBE, and produced nearly stoichiometric amounts of TBA as a terminal product. It was reported also that MTBE was not degraded by resting cells of two anaerobic bacteria, *Acetobacterium woodii* and *Eubacterium limosum*, which, however, were effective in degrading several un-branched ethers. The authors of the study concluded that MTBE was recalcitrant to both aerobic and anaerobic biodegradation.

In view of the state of the art, it is clear that there is a need for technology that will provide the means for a rapid, efficient and cost effective process for converting MTBE and other environmentally undesirable ether-based compounds into environmentally acceptable compounds.

SUMMARY OF THE INVENTION

In accordance with the present invention, there is provided a method for degrading an ether comprising contacting said ether with a propane-oxidizing microorganism or with an isopropanol-oxidizing microorganism.

Examples of preferred species of a propane-oxidizing microorganism are *Mycobacterium vaccae* JOB5, ATCC 29678; Strain ENV420; Strain ENV421; and Strain ENV425.

Also, in accordance with the present invention, a co-substrate is utilized with the microorganism to increase the cell population thereof. For this purpose, the microorganism is grown on co-substrates constituting materials such as, for example, ethanol, acetone, butane, isopropanol and typical bacterial growth substrates, for example, Lauria broth.

Another aspect of the present invention includes degrading the ether by contacting it with the microorganism in a bioreactor, for example, a suspended growth bioreactor, such as a membrane bioreactor, a stirred-tank reactor, or a fixed-film bioreactor.

Still another aspect of the present invention includes degrading the ether with the microorganism in situ.

The degradation of ethers in accordance with the present invention can result in the formation of alcohols which are also degraded by the microorganism. Accordingly, the present invention also comprises degrading an alcohol by contacting it with a propane-oxidizing microorganism or with an isopropanol-oxidizing microorganism. For example, the microorganism can convert tert-butyl ether into tert-butyl alcohol (TBA), which is also degraded by the microorganism. The TBA is in turn degraded to carbon dioxide and water.

The present invention provides means for degrading an ether, for example, tert-butyl ethers and/or tert-butyl alcohols efficiently and economically. It can be used to completely degrade these compounds to innocuous compounds, such as $CO_2$ and water. In contrast, the use of prior art techniques result in undesirable degradation products which require further treatment, such as air- or steam-stripping, use of adsorbents such as activated carbon, and large expenditures of energy to burn the contaminant and the associated media. Other advantages of the present invention will become apparent from a consideration of the following detailed description of the invention.

DETAILED DESCRIPTION OF THE INVENTION

Figure 1A:
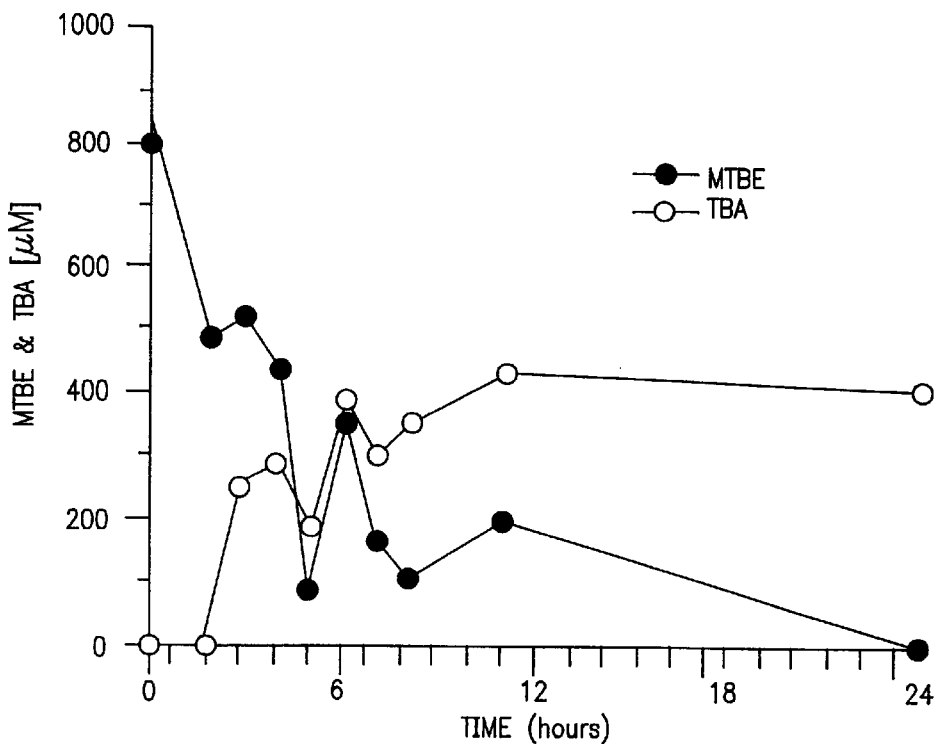
FIG. 1*a* is a graph which shows the degradation of MTBE by propane-grown *Mycobacterium vaccae* JOB5.

The present invention involves the discovery that bacteria capable of oxidizing propane or isopropanol are capable of degrading various types of undesirable ether-based environmental contaminants (also referred to herein as an "ether"). The ether may be aromatic or aliphatic, for example, a cyclic, a straight-chain or a branched-chain ether. Particularly good results have been achieved with ethers that have in their structure a tertiary carbon atom, that is, a carbon atom which does not have a hydrogen atom bonded to it. The tertiary carbon atom is completely substituted, for example, with alkyl groups, including, for example, lower alkyl groups, that is, alkyl groups having 1 to about 5 carbon atoms.

Examples of such ether-based environmental contaminants are compounds used as gasoline oxygenates or solvents, in particular, tertiary alkyl ethers, such as the gasoline oxygenates methyl tert-butyl ether ("MTBE"), ethyl tert-butyl ether ("ETBE") and methyl tert-amyl ether ("MTAE", but referred to commonly as "TAME"). Other types of ether-based compounds which can be treated in accordance with the present invention include saturated cyclic ethers, such as tetrahydrofuran, a material which is widely used in solvents and in chemical bulk products. A mixture of two or more ethers can also be treated in accordance with the present invention. Such ethers can be completely degraded by propane- or isopropanol-oxidizing bacteria.

The present invention involves, additionally, the discovery that degradation products of ethers which are treated in accordance with the present invention and which include —OH groups, can also be degraded utilizing the bacteria described herein. Tert-butyl alcohols ("TBA") are examples of such materials. In general, the present invention is effective in degrading an ether completely to carbon dioxide and water and such degradation can be effected through an intermediate compound, for example, an alcohol.

It is believed that the present invention will be used widely to degrade MTBE which is by far the most common compound used as a gasoline oxygenate. MTBE is a volatile, flammable, colorless liquid at room temperature and has a terpene-like odor. It is miscible in gasoline and is soluble in water, alcohol and other ethers.

A wide variety of materials in which the ether is present may be remediated or decontaminated in accordance with the present invention. Examples of such materials include soils, sludges, sediments, dredge tailings, contaminated gasses, chemical waste and the like. It is believed that the most widely used application of the present invention will involve the treatment of contaminated water, in particular, contaminated groundwater present in urban aquifers and wells.

Methods for determining if a given media is contaminated are well known in the art and include gas and liquid chromatography. For example, MTBE can be detected by gas chromatography according to the EPA method 8260B as described in US EPA publication SW846 US EPA 1986; Test methods for evaluating solid wastes, United States Env. Protection Agency Pub. No. SW 846. Other methods for detecting contamination, such as high performance liquid chromatography (HPLC) may be used, if desired.

The desired extent to which the contaminated material is decontaminated of the ether will usually be defined on a site-specific and material-specific basis. The level of remediation performed at a given site will depend on the intended or actual use of the material contaminated. In most situations, it is desirable to lower the concentration of the ether-based environmental contaminant to levels as low as possible. For example, in treating contaminated water, it would be desirable to reduce the ether-based contaminant concentration to below a level at which the ether is detectable by odor and taste. Thus, in situations where MTBE is present in water that may be used for cooking, drinking or bathing, it would be desirable to lower the level of MTBE to at least below the maximum drinking water level of between 540 and 700 ppb. Lower levels can be achieved, for example, to levels below MTBE's average taste threshold of about 134 ppb, and even below MTBE's odor threshold in water of 45–95 ppb.

Many states have their own standards on the level of contamination that is acceptable in groundwater. In general, the levels of allowable contamination in groundwater are set at about 70 to about 700 ppb. The present invention is capable of being used to degrade the ether-based contaminants to levels at least below current environmental standards.

Microorganisms for use in the practice of the present invention include a propane-oxidizing or an isopropanol-oxidizing microorganism or a mixture of these microorganisms. A method for identification of strains of propane-oxidizing or isopropanol-oxidizing microorganisms capable of degrading ethers is described below in Examples 1, 2 and 3 of the present application.

Propane-oxidizing bacteria that produce a propane monooxygenase ("PMO") enzyme are known to be able to oxidize a variety of substrates including, propane, trichloroethylene, and hydrochlorofluorocarbons (see respectively: Perry, "Substrate Specificity in Hydrocarbon Utilizing Microorganisms, *Antonie van Leeuwenhoek*, 27–36 (1968); L. P. Wackett et al., *Applied and Environmental Microbiology* 55:2960–2964 (1989); and Envirogen Inc. (the assignee hereof, unpublished results). The initial oxidation of the substrates is facilitated by PMO which incorporates a single oxygen atom into the substrate molecule.

Propane-oxidizing bacteria for use in accordance with the present invention include species that produce PMO. It is believed that PMO is the enzyme primarily responsible for degradation of the tertiary butyl ethers, tertiary butyl alcohols and tetrahydrofuran. Accordingly, microorganisms which possess the gene for propane monooxygenase can be used in the practice of the present invention. It is anticipated that microorganisms which are genetically engineered to possess the PMO gene can be used also in the practice of the present invention.

In preferred embodiments of the present invention, the propane-oxidizing microorganisms *Mycobacterium vaccae* JOB5, ENV420, ENV421 or ENV425 are used to degrade ethers, including tertiary butyl ethers, for example, MTBE.

*Mycobacterium vaccae* JOB5 is a known bacteria that is available to the public (ATCC identification number 29678).

Developmental work associated with the present invention has included isolation of the three bacterial strains, namely, ENV420, ENV421 and ENV425.

The strain ENV425 was deposited with the ATCC on Jul. 2, 1996. This microorganism is available to the public in accordance with the terms of the Budapest Treaty. ENV425 is a gram-positive, acid-fast filamentous organism that forms red to orange colonies on BSM or rich media and has been identified by fatty acid analysis to be a member of the genus Nocardia.

Strain ENV420 is also a gram-positive acid-fast filamentous organism. Although similar to Nocardioform bacteria, its fatty acid profile is not a good match with any bacteria present in currently available fatty acid reference databases.

ENV421, like ENV420, appears to be a Nocardioform bacteria whose fatty acid profile does not match any other in currently available fatty acid databases.

The present invention includes within its scope the use of mutagenesis to improve the ability of the microorganisms to degrade a given contaminant or to survive in a given contaminated medium. Standard bacterial mutagenesis techniques known in the art may be employed to mutagenize the bacteria. Alternatively, the bacteria may be modified using genetic engineering to add or delete given genes that effect the bacteria's ability to degrade a given contaminant.

The present invention includes also within its scope the use of one or more other microorganisms in combination with one or more of the microorganisms described herein to achieve complementary degradation against a mixture of contaminants which includes an ether, for example, in the treatment of mixed waste streams. Such a combination utilizes the different degradative specificities of the involved microorganisms. Accordingly, for certain applications, a given contaminated medium may be treated with microorganisms having different specificities for given contaminants or their degradative intermediates.

In applications in which the contaminated site comprises mainly one or more ethers, satisfactory results can be achieved utilizing microorganisms that comprise approximately 100% of propane-oxidizing or isopropanol-oxidizing microorganisms or a mixture thereof. Accordingly, a pure culture of a propane-oxidizing or isopropanol-oxidizing microorganism can be introduced to the contaminated media for remediation. Alternatively, other microorganisms capable of degrading the contaminant or its degradative by-products can be used. In some instances, the growth of such other microorganisms may be aided by the presence of the propane-oxidizing or isopropanol-oxidizing microorganisms which are introduced as a pure culture. For most applications involving mainly an ether contaminant, it is recommended that the propane- or isopropanol-oxidizing microorganisms comprise at least a majority of the degradative microorganisms initially present during remediation. Thus, propane-oxidizing and/or isopropanol-oxidizing microorganisms will constitute greater than 50% of the microorganisms which are present in the contaminated media and which are capable of participating in the degradation of the contaminant(s).

Any suitable carbon source and suitable conditions can be used to increase the cell population of the involved microorganisms. Such increase is referred to herein as "growth of the microorganisms" and materials for use in effecting the growth are often accompanied by use of the term "grown on". For example, the propane-oxidizing and the isopropanol-oxidizing bacteria may be grown on propane and isopropanol, respectively. Such compounds can serve as the exclusive source of carbon for the microorganism.

There are applications in which it can be advantageous to use other materials to grow the propane-oxidizing microorganisms and/or the isopropanol-oxidizing microorganism. In this connection, it is noted that propane is a flammable gas. For certain applications, it may be more convenient and practical to use a liquid carbon source, instead of propane, for growing the propane-oxidizing microorganism. Examples of liquid carbon sources for such microorganisms are isopropanol, acetone, and ethanol. On the other hand, another example of a gas which may be used as the carbon source is butane.

Conventional bacterial growth media can also be used to effect an increase in cell population. Examples of such growth media are: Lauria broth (Gibco/BRL); Trypticase soy agar (BBL; Bectin/Dickinson, Cockysville, Md.); R2A (Difco Laboratories, Detroit, Mich.); and nutrient broths, including casamino acids and/or yeast extract.

Once the cell population has reached a desirable level, it may be desirable to transfer the cells to a growth media which promotes expression of the genes responsible for degradation of the contaminant. For example, as mentioned above, it is believed that propane monooxygenase ("PMO") is primarily responsible for the degradation of ether-based contaminants. To promote the expression of the PMO gene, there can be used a growth medium comprising basal salts (minimum) and either propane and/or isopropanol as an inducer of the propane monooxygenase gene and as a carbon source. If desired, the techniques of molecular biology may be used to screen for compounds which induce expression of the PMO gene.

Growth of the bacteria can be effected in a bioreactor or in situ and can be enhanced by the addition of growth substrates which are more readily metabolized by the microorganisms.

A media which is contaminated with an ether-based compound and/or the degradation products of these ethers can be contacted with propane- or isopropanol-oxidizing bacteria either at the site of contamination or by transferring the contaminated media to a bioreactor for remediation off-site.

A variety of bioreactors known to those of skill in the art may be used in the practice of the present invention. Suspended growth reactors, such as membrane bioreactors, standard continuously stirred tank reactors (CSTRs) and activated sludge systems may be used in the practice of the invention. Alternatively, and because bacteria adhere strongly to surfaces, fixed film reactors, such as fluidized bed reactors or fixed support reactors, may also be used, if desired.

It is believed that a suspended growth reactor, in particular, a membrane bioreactor, will be particularly efficient. An example of a membrane bioreactor is presented in FIG. 7. The membrane bioreactor system consists of a tank or reactor vessel 10 equipped with a variable speed mixer, an air diffuser, an automated pH controller and nutrient 12 and acid/caustic feed 14 systems. Groundwater 15 or other contaminated liquid media is introduced from an equalization tank 16 via a reactor feed pump 18. If desired, filtered dilution water 17 may be added to the equalization tank. Effluent from the reactor vessel 10 is passed through membrane filters 20 which retain the microorganisms present in the reactor vessel 10 but allow the effluent containing the degradation products of the ether to pass.

Effluent from the bioreactor may be sent to a proof tank 22 which is used to hold the effluent so that it can be analyzed before passing the effluent along to a holding tank 24 and subsequently discharging into the sewer system 28.

Soda ash, caustic solutions containing, for example, NaOH or KOH, or acids may be used to control pH and soluble fertilizer may be used to supply nutrients to the microorganisms. In preferred embodiments, the fertilizer or other nutrient source supplies nutrients at a ratio of about 100 parts carbon to about 10 parts nitrogen to about 1 part phosphate (100:10:1). Examples of fertilizer acceptable in the practice of the present invention include fish oil emulsion or any other soluble agricultural fertilizer, such as Agway 20—20—20 or Lesco 19—19—19, ammonium chloride or ammonium nitrate-based fertilizers and potassium or sodium phosphate-based fertilizers. The liquid level in the reactor may be controlled by equipment available in the art designed to maintain reactor liquid volume.

When a membrane bioreactor is used, effluent from the reactor may be passed over ultrafiltration membranes or other filtration apparatus. An example of an ultrafiltration membrane useful in the practice of the invention is Rhone-Poulenc Model SC37/K09.

Operation of the bioreactor will usually have two phases: an initial batch operation and then continuous operation. Batch operation is used to produce large amounts of degradative biomass within the reactor system, and to acclimate the degradative organisms to the contaminant feed. The following description is illustrative of an operation involving the use of a propane-oxidizing bacteria.

Batch operation can be initiated by inoculating the reactor with the propane-oxidizing microorganism and then adding isopropanol, for example, to a final concentration of from 0.1 to 1% (v/v). The organisms are aerated and allowed to grow until no isopropanol remains in the culture medium. Additional isopropanol can then be added to further increase biomass levels. After sufficient biomass is obtained, a small amount of contaminant (e.g., MTBE) can be added to acclimate the organisms. Additional contaminant can be added after depletion of the prior addition. When sufficient degradation rates are achieved, the reactor can be operated in a continuous mode.

Preferably, during continuous and batch operation, the reactor should be operated at a temperature of between 25 and 37° C., with the pH in the range of 6.8 to 7.2, and a dissolved oxygen concentration >5 mg/L. Hydraulic retention time within the reactor should be adjusted to allow sufficient time for degradation of the target compound to below treatment standards. During field and laboratory testing, a hydraulic retention time of 2.5 to 3.3 days was sufficient to degrade >90% of influent MTBE. Furthermore, the volatile suspended solids (biomass) concentration should be maintained at a relatively high concentration, preferably from 1,000 to 30,000 mg/l depending on the contaminant loading rate.

In certain circumstances, it may be more convenient or economical to treat a contaminated site in place (in situ). The following description is illustrative of an operation involving the degradation of gasoline oxygenates.

Most environmental contamination by gasoline oxygenates occurs in the subsurface—either in the unsaturated (vadose) or saturated zones of soils. Gasses can be added readily to the subsurface either by injection/vapor extraction (vadose zone) or by in situ gas sparging (saturated zone) (Marley, M.C., E.X. Droste, H.H. Hopkins, and C.J. Bruell, 1996, Use Air Sparging to Remediate, *Environ. Engineer. World*, March–April 1996, 6–14). When the techniques are used to stimulate the growth and activity of natural pollutant degrading microorganisms, they are referred to "bioventing" and "biosparging", respectively, and "biostimulation" collectively. It is, therefore, possible to perform in situ remediation of gasoline oxygenates by injecting gaseous co-substrates (e.g., propane or butane and air) into the subsurface to stimulate biodegradation of gasoline oxygenates by naturally-occurring propane and/or butane oxidizing bacteria. The use of gas (methane) injection to remediate aquifers contaminated with trichloroethylene has been demonstrated. See, for example: (A) Lombard, K. H., J. W. Borthen and T. C. Hazen, 1994, The design and management of system components for in situ methanotrophic bioremediation of chlorinated hydrocarbons at the Savannah River Site, in: R. E. Hinchee (ed.), *Air Sparging for Site Remediation*, Lewis Publishers, Boca Raton, Fla., pp. 81–96; and (B) Hazen, T. C. et al., 1994, Summary of in situ bioremediation demonstration (methane biostimulation) via horizontal wells at the Savannah River Site Integrated Demonstration Project, in: *In Situ Remediation: Scientific Basis for Current and Future Technologies*, Battelle Press, Richland, Wash., pp. 137–150.

In a standard air sparging method, clean air is injected into an aquifer beneath the water table. Volatile organic components dissolved in the groundwater are forced into the vapor phase due to mass transfer. The contaminated vapors migrate from the saturated portions of the aquifer to the unsaturated or "vadose" zone above the water table. Migration of the organic vapors from the aquifer to the vadose zone may be controlled by soil vapor extraction (SVE) techniques. SVE usually employs vacuum pumps located at the surface connected to vapor extraction wells which pass through the vadose zone and which draw the contaminated vapors to the surface. The extracted vapors are then treated using a variety of ex situ treatments schemes including carbon absorption, catalytic oxidation, biofiltration or condensation.

The techniques of in situ air sparging can readily be adapted to the treatment of an area contaminated with an ether-based compound, such as MTBE. In particular, rather than injecting clean air, a gas, such as propane, can be added readily to the subsurface either by injection/vapor extraction (vadose zone) or by in situ gas sparging (unsaturated zone). Injection/vapor extraction is effective in treating the vadose (unsaturated) zone of the subsurface, and relies on gaseous diffusion of added substrates (e.g., propane and air) through the unsaturated soils. Soil vapor extraction is used to direct the flow of the added gasses, and to remove and capture any volatile contaminant. In many cases, depending on the composition of the soils, this method allows treatment of large areas of contaminated soils at a low cost. In situ gas sparging involves injecting gaseous substrates (e.g., propane and air) directly into the saturated zone of the subsurface. This process facilitates the dissolution of the substrates into the aqueous phase of the aquifer, thereby allowing indigenous or added organisms the aquifer, thereby allowing indigenous or added organisms to use the substrates as a source of energy for growth and degradation.

Vapor extraction can be coupled with in situ sparging to capture gasses which do not completely dissolve into the aqueous phase. In effect, injection/vapor extraction allows remediation of the unsaturated zone of the subsurface by stimulating degradative organisms in the unsaturated soil, whereas in situ sparging allows remediation of the saturated zone of the subsurface by stimulating organisms in the aqueous phase of the aquifers or attached to the saturated soils. Accordingly, in situ remediation of a given ether-based contaminant, such as MTBE, may be accomplished by injecting gaseous co-substrates, such as propane or butane and air into the subsurface to stimulate the biodegradation of the ether by naturally-occurring propane and/or butane oxidizing bacteria.

Alternatively, the microorganisms disclosed in the present invention may be added in situ at the site of the contamination, followed by the provision of propane or butane and air to stimulate the growth and activity of these introduced microorganisms.

Typically, microorganisms which are to be used for in situ remediation are cultured, that is, grown in fermentors to high cell density (>$1 \times 10^{10}$) under conditions that induce production of degradative genes (e.g., in the presence of propane). The organisms can then be concentrated by centrifugation or ultrafiltration, or they can be shipped directly to location of injection. Alternatively, cultures of the organisms can be grown directly on site and injected batch-wise or continuously into the contaminated media. The microorganisms can be diluted prior to injection, or injected in a concentrated form. Ideally, the final concentration of the organisms in the contaminated media will be from about $1 \times 10^7$ to about $1 \times 10^9$ cells/ml (gm) of contaminated media. Alternatively, the organisms can be injected at a lower initial concentration (e.g., $1 \times 10^5$ cells/ml) and additional growth substrate can be added to promote growth of the organisms within the contaminated media.

Injection of the organisms can be achieved by adding the organisms to an injection well composed of suitable pipe screened in the desired injection zone, or into a re-injection injection stream of water removed from one location of the aquifer and re-injected into another area. The microorganisms can also be injected in an air or fluid stream used to facilitate fracturing of consolidated aquifer materials by processes known in the art, such as pneumatic or hydraulic fracturing, respectively.

To perform in situ bioremediation, a preferred system involves use of small diameter wells of approximately 1 to about 4 inches in diameter which are drilled at the site of the contamination, with the bottom portion of the well located several feet below the water table. The injection rates of the desired gas will vary depending on the type of gas and the nature of the soil or other media surrounding the well. However, in general, a gas flow rate of a few cubic feet per minute, preferably greater than about 10 to about 15 CFU/min is utilized. When injecting a given gas into a saturated aquifer, sufficient pressure will be required to overcome the sum of the hydrostatic pressure of the overlying groundwater in the air and entry pressure of the underground soil or sediment formation.

Guidance on the parameters for determining the appropriate flow rates for inducing a gas in an air sparging system and construction of air sparging systems may be found in a variety of publications, including, "Use of Air Sparging to Remediate," by M. C. Marley et al., *Environmental Engineering World*, March–April 1996; "Removing Gasoline from Soil and Groundwater Through Air Sparging," by Michael C. Marley, *Remediation*, Spring 1992; and "Successfully Applying Sparging Technologies," by Michael C. Marley and Edward X. Droste, *Remediation*, Summer 1995. The information in these publications may be adapted for use in the present invention by replacing air with the desired gas, such as propane. In the case of the propane-oxidizing bacteria which have been found to be useful in the practice of the present invention, air, oxygen, propane and/or butane may be injected into the subsurface by inserting the injection wells into either the vadose or saturated zones. Vapor extraction wells can then be inserted into the vadose zone to capture the gases and direct the flow of gas within the subsurface. Co-substrates such as propane and/or butane and air oxygen can be injected simultaneously or by pulsing in one co-substrate followed by another. As an example, propane or butane can be injected for 4 hours, followed by injection of oxygen for 4 hours.

The concentration of MTBE or other contaminant in the contaminated zone can be monitored by analyzing the gas recovered in the vapor extraction system or by monitoring liquid phase concentrations of the contaminant in the groundwater. Quantification of the increase in numbers of oxidizing bacteria may be monitored by recovering soil or water samples from the subsurface and spreading samples on the surface of BSM agar plates. Plates are incubated in a sealed jar containing an atmosphere of the gaseous growth medium and air. Colonies of oxidizing bacteria are enumerated by counting the colonies that form on the plates.

EXAMPLES

The following examples are illustrative of the practice of the present invention and demonstrate its use to degrade effectively MTBE and TBA. The examples include degradation of MTBE in a bioreactor and degradation of MTBE in situ.

Bacterial Strains and Growth

The bacterial strains ENV420, ENV421 and ENV425 are examples of propane-oxidizing bacteria isolated from environmental samples. The organisms were isolated from soil by adding approximately 1 g of soil to a 250 ml Erlenmeyer flask containing 100 ml of basal salts media ("BSM"; Hareland, W., R. L. Crawford, P. J. Chapman, and S. Dagley. 1975. Metabolic function and properties of 4-hydroxyphenylacetic acid 1-hydroxylase from *Pseudomonas acidovorans*. J. Bacteriol. 121:272–285). The flasks were sealed with rubber stoppers that were pierced with an 18 gauge needle. The needle was fitted with a sterile filter unit (Nalgene, cat. no. 190–2520; 25 mm diameter; 0.2µM pore size) and a three-way stopcock was fitted to the top of the filter unit. A vacuum was applied to the needle assembly to remove air from the flask headspace and 60 ml of propane were injected through the stopcock and filter into the flask. The stopcock was opened briefly to allow air to flow into the flask and to reach atmospheric pressure. The flasks were then incubated at room temperature with constant shaking (200 rpm) to allow growth of propane-oxidizing bacteria.

Once visible growth was observed in the flasks, a portion of the culture was removed and placed into a similar vessel containing sterile BSM and the incubation was repeated. After three such transfers, a portion of the culture was diluted with fresh BSM and plated onto BSM/agar plates. The plates were inverted and incubated in a sealed jar containing an atmosphere of 20% propane in air. The gasses within the sealed jars were replaced periodically with a fresh gas mixture, and the plates were incubated until colonies appeared. Individual colonies were streaked on fresh BSM/agar plates and grown on propane to insure purity of the culture. Once pure cultures were obtained, colonies of the bacteria were transferred to flasks and grown in propane as described above.

Strain ENV420 is a gram positive rod. Strain ENV421, like ENV420, appears to be a Nocardioform bacteria whose fatty acid profile does not match any other in currently available fatty acid databases. Strain ENV425 is a gram positive rod that forms red to orange colonies on BSM or rich media.

The propane-oxidizing bacteria *Mycobacterium vaccea* JOB5 was obtained from the ATCC (ATCC identification number 29678) and grown on a rich media PTGY media or on BSM plus propane as described above. One liter of PTGY media contains: 1 g glucose; 1 g yeast extract; 0.5 g peptone; 0.5 g tryptone; 0.6 g magnesium sulfate (7-hydrate); 0.07 g calcium chloride (anhydrous); and 17 g of bacto agar.

To test the ability of the propane-oxidizing bacteria to grow on other substrates, various test strains were grown on BSM plus isopropanol, BSM plus ethanol or BSM plus acetone. To grow the cells on BSM plus isopropanol, ethanol or acetone, the cells were placed into BSM containing from 0.1 to 1% (v/v) isopropanol, ethanol, or acetone and incubated at 25° to 30° C. with constant shaking. Alternatively, the cells were streaked onto BSM/agar plates containing 0.1 to 1% isopropanol, ethanol, or acetone and incubated in an inverted position until colonies formed. The growth rate of the cells on BSM with either propane, propanol, ethanol, or acetone could be enhanced by the addition of casamino acids (0.02%) or yeast extract (0.02%) to the growth media. Cell growth was measured by monitoring the optical density of the culture at 550 nm ("$OD_{550}$") in a Spectronics 20 spectrophotometer.

Gas Chromatography Assay for Methyl-tert-Butyl Ether, Ethyl-tert-Butyl Ether, and tert-Butyl Alcohol Degradation Propane-oxidizing microorganisms were grown as described above on either propane, isopropanol, ethanol or acetone, to a cell density of $OD_{550} \geq 0.5$. The cells were then collected by centrifugation, washed with BSM, and suspended to an $OD_{550}$ of 1.0. Five ml of cell suspension were placed into 10 ml serum vials and MTBE, ETBE, or TBA dissolved in distilled water was added to a final concentration of 5 to 100 mg/L (ppm). The vials were sealed with Teflon-lined septa and crimp seals and incubated with shaking (250 rpm) at 30° C. for at least 24 hr. Control samples were prepared by adding 50 µl of 10 mM $HgCl_2$ to replicate vials. $HgCl_2$ killed the microorganisms present in the vials allowing these vials to serve as controls. At pre-determined time points, 50 µl of 10 mM $HgCl_2$ were added to the incubating sample to stop the reaction or a sub-sample of the incubating sample was removed for analysis. Degradation of MTBE, ETBE or tert-butyl alcohol (TBA) was measured by gas chromatography.

Gas chromatography was performed by first removing cells from the samples by centrifugation of the sample vial or the sub-sample. A pre-sealed 2-ml autosampler vial was partially evacuated by inserting a syringe needle through the septa and removing 500μl of air. Five hundred μl of the clear supernatant fraction of the cell culture were then injected into the vial. The samples were then analyzed by injecting 1 μl of the sample directly into a Varians Model 3400 gas chromatograph equipped with a 30m Vocol capillary column (Supelco) and a flame ionization detector. The column, injector, and detector were maintained isocratically at 80° C., 200° C., and 225° C., respectively. Standard curves of each compound were generated with aqueous standards of 10 ppm, 25 ppm, 50 ppm, and 100 ppm. The retention time of the target compounds were: MTBE, 0.75 min; TBA, 0.68 min; and ETBE, 8.04 min.

Example 1

The ability of three propane-oxidizing bacterial strains to degrade MTBE, ETBE and TBA after growth on various substrates is presented in Table 1. To perform these studies, cells were grown in BSM on the listed substrate, washed, suspended in BSM to an optical density at 550 nM of 1.0, and incubated for 24 hours with 30 mg/l of either MTBE, TBA or ETBE. Gas chromatography analysis, as described above, was used to quantitate the percentage of MTBE, TBA, or ETBE degraded during the 24-hour time period.

TABLE 1

| Strain | Growth Substrate | % MTBE Degraded | % TBA Degraded | % ETBE Degraded |
| --- | --- | --- | --- | --- |
| M. vaccae JOB5 | propane | 100 | 45 | 100 |
| | isopropanol | 93 | 11 | 80 |
| ENV420 | propane | 50 | 10 | 0 |
| | ethanol | 86 | 56 | 31 |
| ENV425 | propane | 67 | 23 | 26 |
| | isopropanol | 71 | 0 | 14 |

Example 2

FIG. 1a shows the degradation of MTBE by propane-grown *Mycobacterium vaccae* JOB5 (ATCC 29678). The strain degraded 100% of the added MTBE (518 μM; 46 ppm) within 24 hr. Biodegradation of MTBE resulted in the transient accumulation of TBA which is subsequently degraded by the microorganism. MTBE was not degraded by cultures that had been poisoned with $HgCl_2$.

Example 3

Figure 1B:
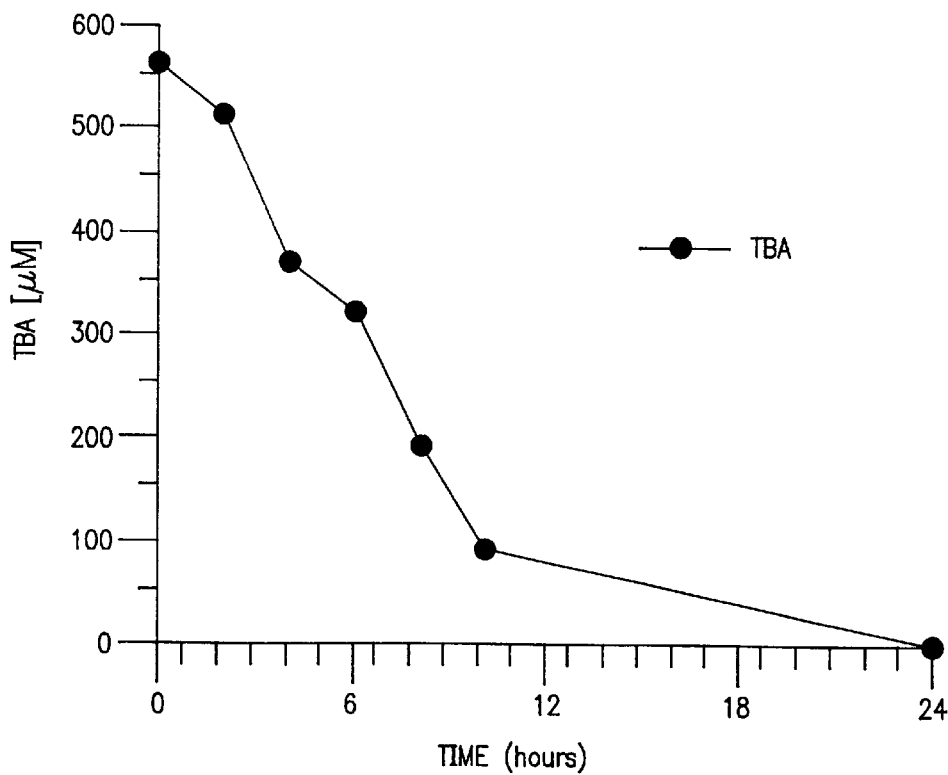
FIG. 1*b* is a graph which shows the degradation of TBA by propane-grown Mycobacterium JOB5.

FIG. 1b shows the degradation of TBA by propane-grown *Mycobacterium vaccae* JOB5 (ATCC 29678). The strain degraded 100% of the added TBA within 24 hr. No TBA was degraded by $HgCl_2$-poisoned cells.

Degradation of MTBE by ENV425 and ENV420 following growth on ethanol or propane was measured chromatographically and the results are presented in FIGS. 2 through 5.

Example 4

Figure 2:
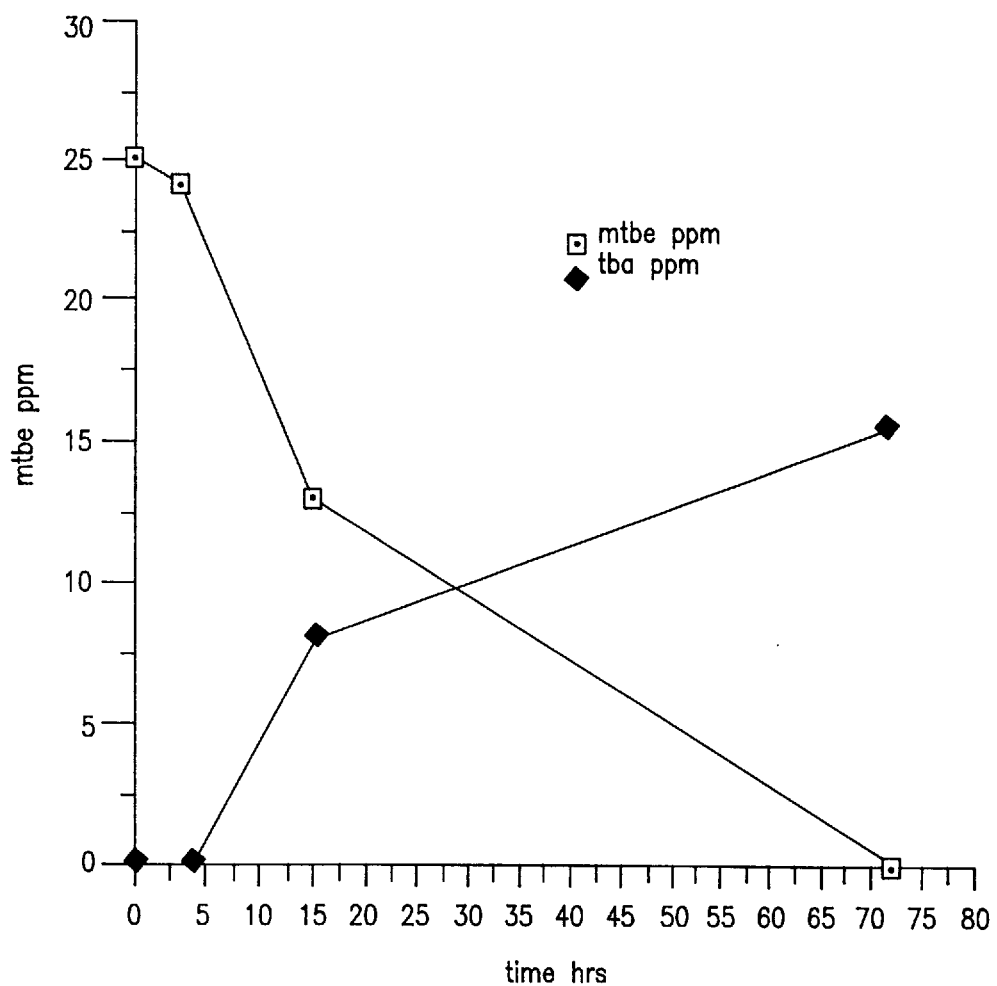
FIG. 2 is a graph which shows the degradation of MTBE by strain ENV425 after growth on ethanol.

FIG. 2 shows degradation of MTBE by Strain ENV425 which was provided with ethanol as the sole carbon and energy source.

Example 5

Figure 3:
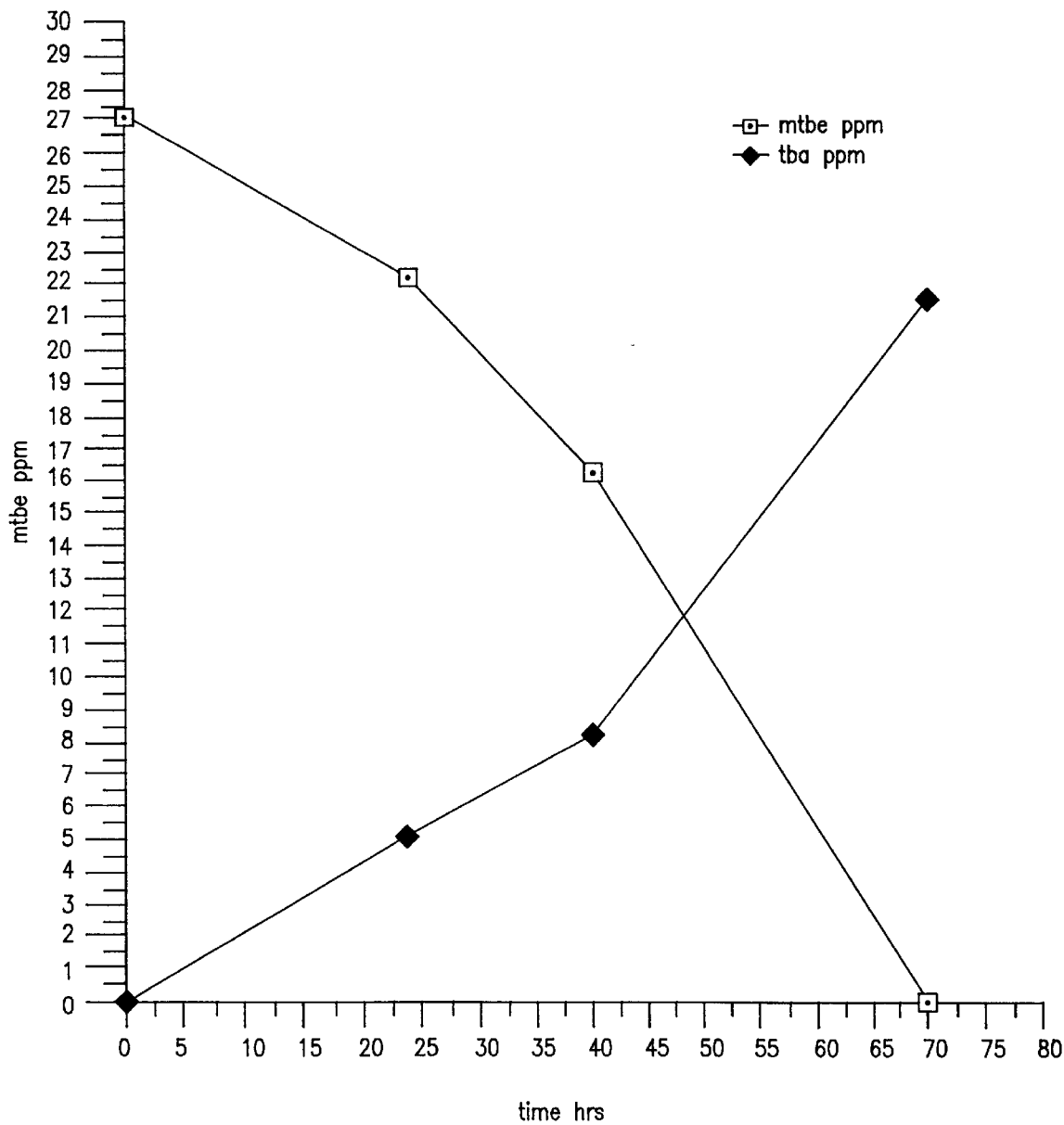
FIG. 3 is a graph which shows degradation of MTBE by strain ENV420 after growth on ethanol.

FIG. 3 shows degradation of MTBE by strain ENV 420 which was provided with ethanol as the sole carbon and energy source.

Example 6

Figure 4:
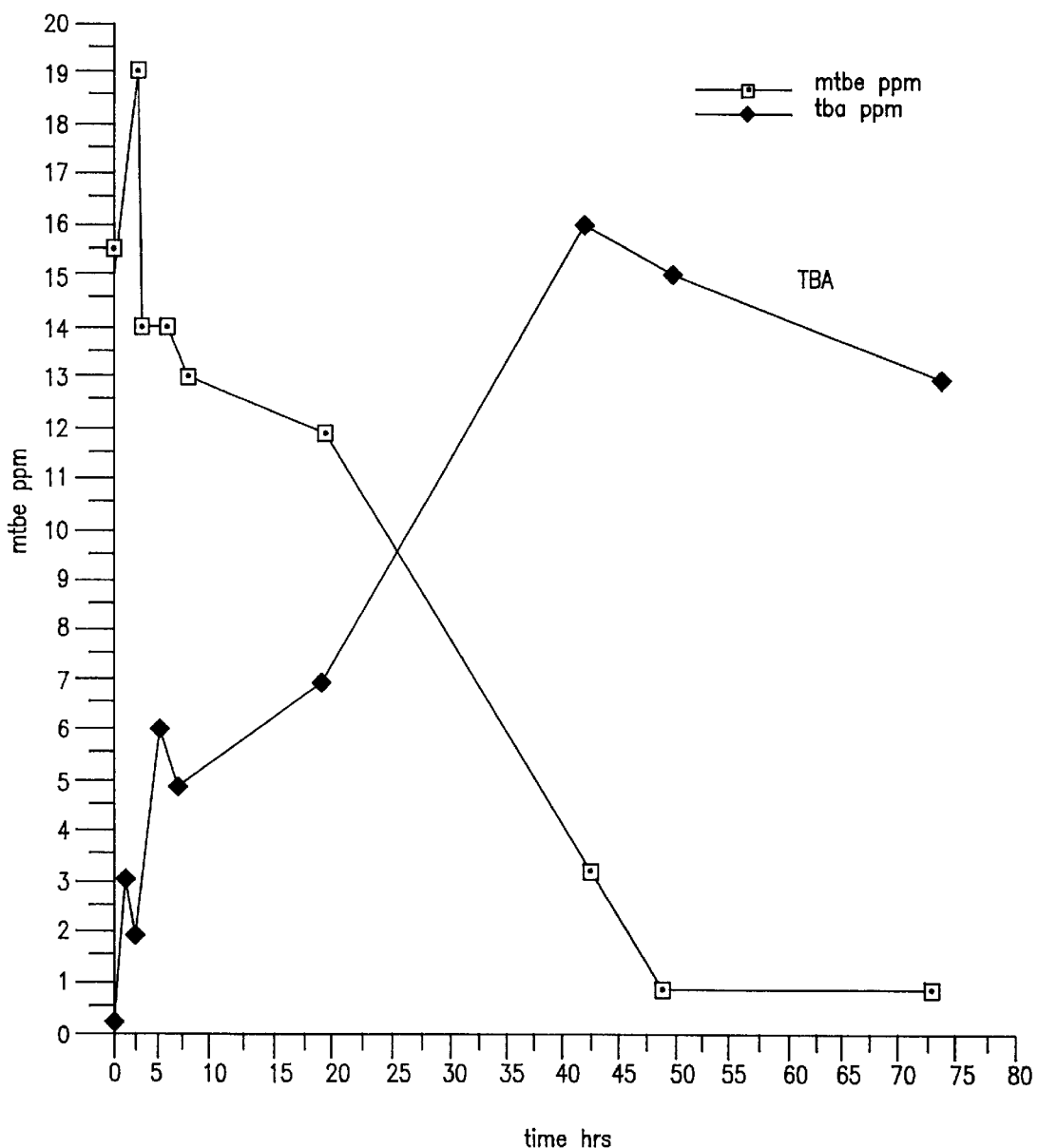
FIG. 4 is a graph which shows degradation of MTBE by strain ENV420 after growth on propane.

FIG. 4 shows degradation of MTBE by Strain ENV420 which was grown with propane as the sole carbon and energy source.

Example 7

Figure 5:
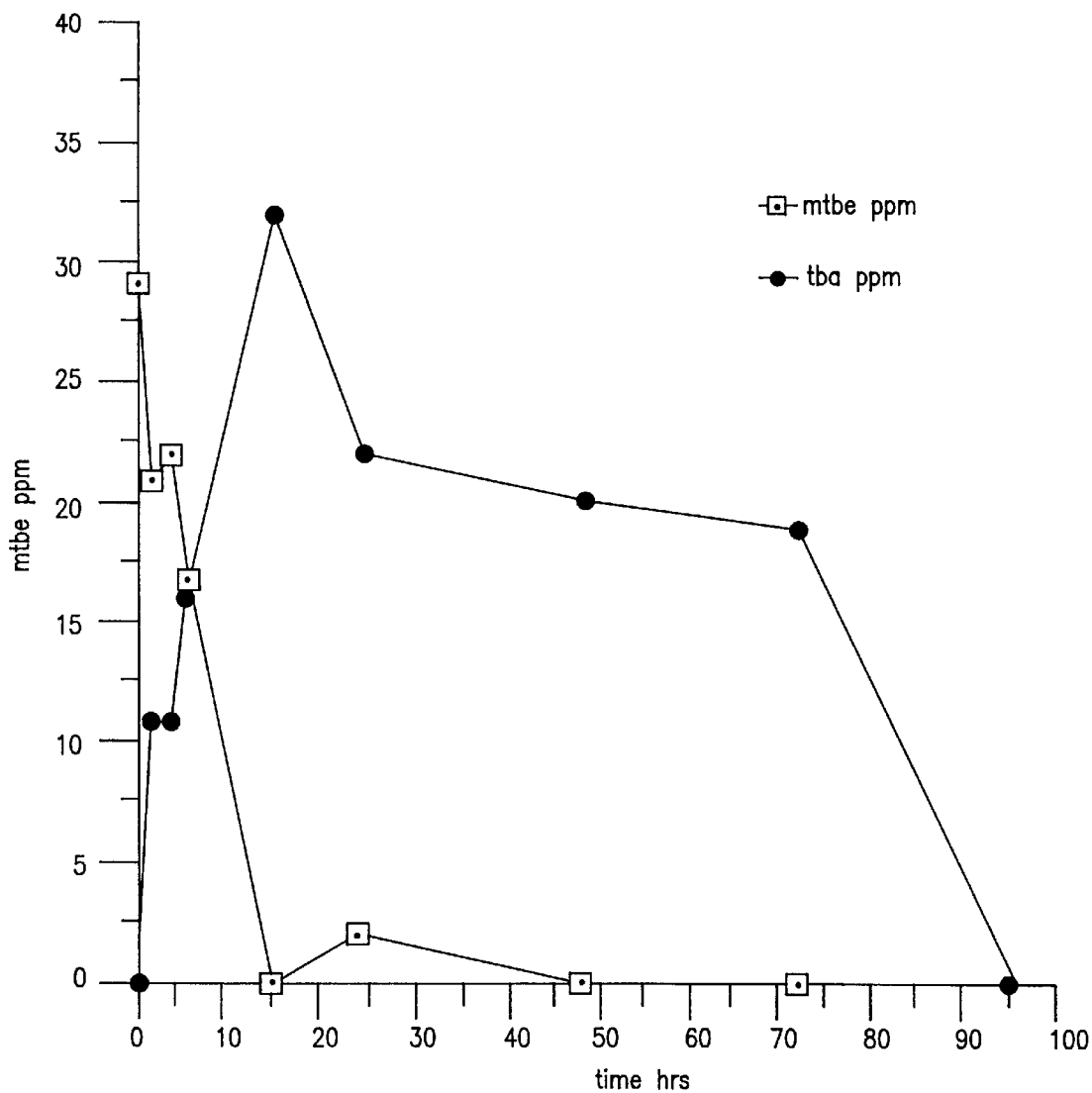
FIG. 5 is a graph which shows degradation of MTBE by strain ENV425 after growth on propane.

FIG. 5 shows degradation of ETBE by Strain ENV425 which was grown with propane as the sole carbon and energy source.

The next two examples illustrate also the degradation of MTBE by propane-oxidizing bacteria and include an assay that shows that significant portions of the MTBE are converted to $CO_2$.

Examples 8 and 9

[$^{14}$C]MTBE Assay

These examples included the use of propane-oxidizing bacteria that were incubated with radiolabeled MTBE. Assays were performed by preparing propane-grown cells as described above, adding 5 ml subsamples of washed cells to 26 ml serum vials, and amending the same with 1.36 μCi of uniformly labeled [$^{14}$C] MTBE (10.075 mCi/mmol; New England Nuclear Products, Boston, Mass.; Lot No. 3048-175A) in 2.5 μl ethanol. Twenty mg/L of non-labeled MTBE were also added to each vial. The vials were incubated at 25° C. with shaking (100 rpm) and at timed intervals, the samples were analyzed for MTBE, TBA, and radioactive products including $^{14}CO_2$. Analysis of radioactive products was performed as described by Speitel and colleagues (Speitel, G. E., R. C. Thompson, and D. Weissman, "Biodegradation kinetics of *Methylosinus trichosporium* OB3b at low concentrations of chloroform in the presence and absence of enzyme competition by methane," *Water Res.*, 27:15–24 (1993)). Preliminary testing demonstrated that this method produced measurements of $^{14}CO_2$ production that were comparable to methods that rely on trapping $^{14}CO_2$ in an alkaline solution.

To terminate the reactions and to draw gaseous $CO_2$ into the sample liquid, 75 μl of 2N NaOH were injected through the septa. The vials were then returned to the shaker for 30 minutes. After incubation, 100 μl of the culture liquid were removed through the septa, placed in 5 ml of OptiPhas "Hi Safe III" scintillation cocktail (Wallac Scintillation Products, Turku, Finland) and the amount of radioactivity in the sample, as disintegrations per minute (dpm), was determined by liquid scintillation counting in a Wallac 1209 Rackbeta liquid scintillation counter (Pharmacia LKB Nuclear Inc., Gaithersburg, Md.). This basic fraction contained particulate $^{14}$C (cell fraction), dissolved $^{14}CO_2$, and unreacted [$^{14}$C]MTBE. It was used as a measurement of "total" counts recovered. To liberate the dissolved $^{14}CO_2$ from the aqueous phase, 500 μl of 6N HCl were added to the vials and the acidified cultures were incubated for 30 minutes with shaking. A 100 μl aliquot of the culture was then withdrawn through the septa and liquid scintillation counting was performed as described above. This acidic fraction contained soluble $^{14}$C-labeled compounds, but not $^{14}CO_2$. The difference in dpm between the basic fraction and the acidic fraction was a measure of the $^{14}CO_2$ formed from [$^{14}$C]MTBE.

To remove any additional volatile $^{14}$C-labeled compounds from the aqueous phase, the vials were opened and gently agitated overnight. The amount of radioactivity remaining in both the soluble and particulate form was measured by removing 100 μl of the overnight culture for scintillation counting. The remaining culture was then centrifuged to remove the particulate fraction and 100 μl of the supernatant ("soluble" fraction) were removed for liquid scintillation counting. The "particulate" fraction was the difference in activity between the overnight culture and the "soluble" fraction. The total amount of $^{14}C$ activity added was determined by adding 2 μl of the [$^{14}C$]MTBE stock directly to 5 ml of scintillation cocktail and performing liquid scintillation counting.

Table 2 below presents the results of [$^{14}C$]MTBE assays.

TABLE 2

Degradation of [$^{14}C$]MTBE by Propane-Oxidizing Bacteria
Percent of added [$^{14}C$]
in $CO_2$, liquid and particulate fractions[1]

| Strain | $CO_2$ | Liquid | Particulate |
|---|---|---|---|
| M. vaccae JOB5 | 27(2) | 71(2) | 0 |
| ENV425 | 41 | ND | ND |
| TXR[2] | 53(1) | 46(1.5) | 0 |

ND—No data available.
[1]Cells were grown in BSM media with propane, washed, suspended to an optical density at 550 nm of 1.0, and incubated overnight with 0.5 μCi of uniformly-labeled [$^{14}C$]MTBE (2 μM MTBE). Cultures were fractionated as previously described, and the activity in each fraction was quantitated by liquid scintillation counting. Values represent the mean of three samples with standard deviations of the means in parentheses. Cultures of ENV425 were assayed at an optical density of 5.0.
[2]Culture "TXR" was a mixed culture of naturally-occurring propane-oxidizing bacteria recovered from a field pilot-scale bioreactor.

Strain ENV425, strain M. vaccae JOB5, and a mixed culture of natural propane oxidizers ("TXR") converted a significant portion of the added [$^{14}C$]MTBE to $^{14}CO_2$, thereby demonstrating that the cells completely mineralize MTBE to $CO_2$ and water.

The next example shows the use of a laboratory scale bioreactor to degrade MTBE by propane-oxidizing microorganisms.

Example 10
Use of a Laboratory-Scale Membrane Bioreactor for degradation of MTBE To demonstrate the ability of the microorganisms described herein to degrade MTBE in a laboratory-scale bioreactor, cells of strain ENV425 were grown in a 3L Applicon round-bottom fermentor (Cole Palmer) on BSM with 0.1% isopropanol.

The operating volume of media in the reactor was 2.5L. The reactor was fed with BSM containing from 100 to 5000 mg/l MTBE, with or without the addition of an equal concentration of isopropanol to maintain high biomass in the reactor. The BSM feed rate was 1.7 ml/min. to create a hydraulic residence time in the reactor of 2.5 days. The effluent of the reactor passed over the surface of a 100,000 mwt ultra filtration membrane (Model CR250; Raisio Flootek, Molmo, Sweden), at a flow rate of 1.2 to 2.2 ml/min at a pressure of from 1 to 1.5 psi. The retenate containing cells were passed back into the reactor, and the filtrate was discarded as the treated effluent. The reactor was operated at 30° C. at a pH of 7. When the MTBE feed concentration exceeded 3000 mg/L, an additional 300 mg/l of nitrogen in the form of ammonium chloride, were added to the feed solution. Oxygen concentration within the reactor was monitored by using an Ingold pH probe and a Cole Palmer model 01971-00 oxygen monitor, and oxygen concentration was maintained at >1% air saturation by adding air or oxygen directly to the reactor. MTBE concentrations in the feed, reactor, and effluent were determined by gas chromatography as described previously.

Figure 6:
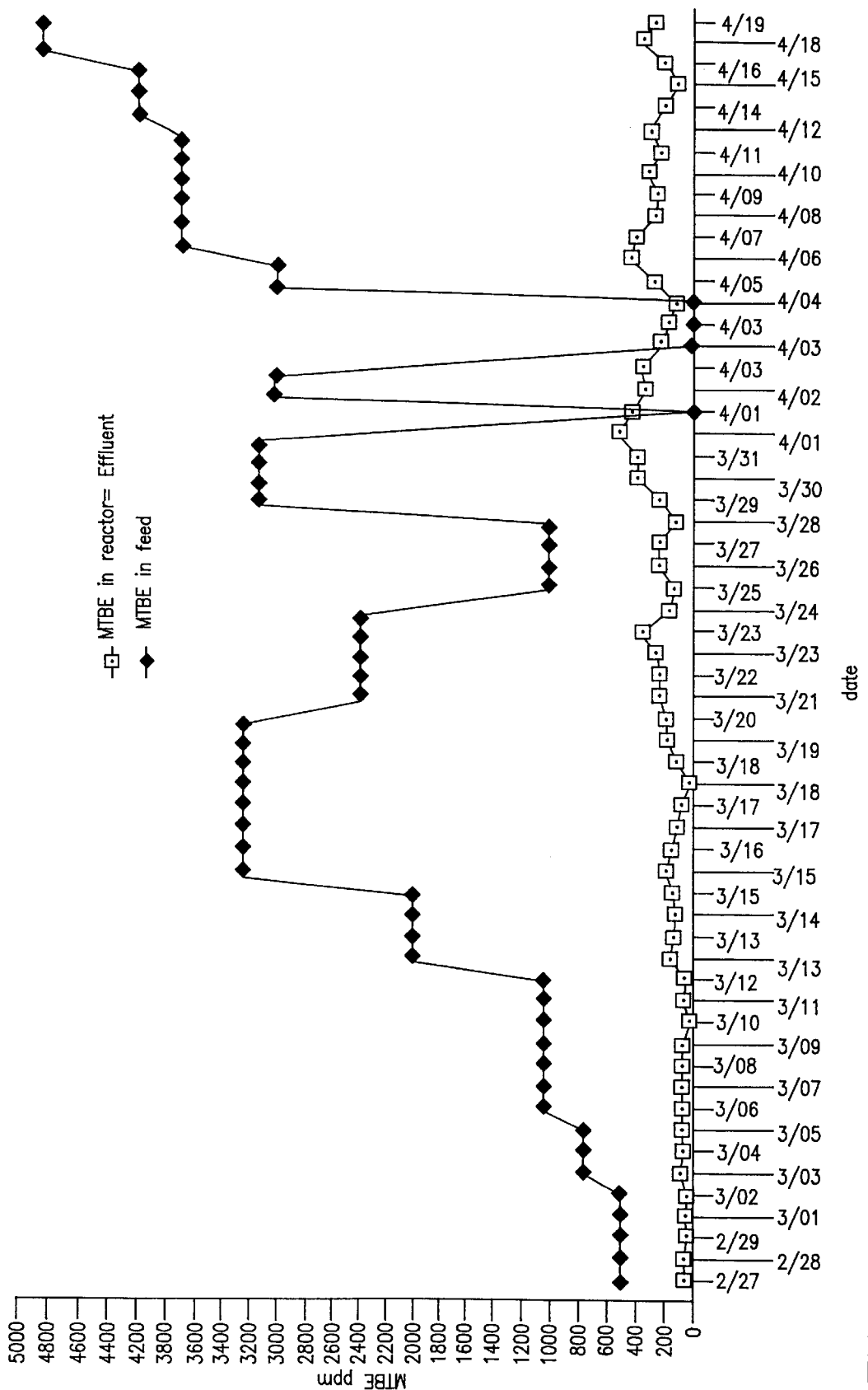
FIG. 6 is a graph which shows the degradation of MTBE over the course of approximately two months in a laboratory reactor.

Results of the laboratory reactor's performance are shown in FIG. 6. Greater than 95% of the MTBE added to the reactor was removed during the 2.5 day hydraulic retention time. The reactor operated successfully for more than 5 months. Measurement of volatile suspended solids, which reflect the biomass present in the reactor showed an increase from an initial concentration of <100 mg/L to more than 2200 mg/L during the treatment period. MTBE stripping from the reactor was typically <5% of the influent MTBE mass.

As mentioned above, previous attempts to treat MTBE in a bioreactor with non-propane oxidizers have involved slow growth of natural MTBE degraders and extremely long (up to 4 months) reactor start-up periods. (Salanitro et al., "Isolation of a Bacterial Culture that Degrades Methyl t-Butyl Ether," Applied and Environmental Microbiology, 2593–2596 (July 1994)). The present invention avoids these prior art problems by providing propane-oxidizing or isopropanol-oxidizing bacteria with an efficient growth substrate, such as propane, isopropanol, acetone or ethanol which enables the microbial population in the bioreactor to rapidly increase to a level where MTBE can be degraded, avoiding the slow growth and resultant start-up lags seen in many bioreactor systems. Furthermore, the ability to grow up the organisms on isopropanol, ethanol or acetone avoids the problems associated with use of propane which is an explosive material.

The ability to use isopropanol as a growth substrate to rapidly increase biomass is illustrated in the next example which shows the use of an industrial-size bioreactor to degrade MTBE by propane-oxidizing bacteria.

Example 11
Use of a Field-Scale Membrane Bioreactor System

Propane oxidizing bacteria were deployed in a field-scale membrane bioreactor (MBR) system to treat MTBE-contaminated groundwater at an oil refinery. An MBR is a type of suspended growth reactor.

The MBR system used in the present example consisted of a 1000-gallon tank equipped with a variable speed mixer, an air diffuser capable of providing up to 600 ft$^3$ of air per hour, an automated pH controller, and nutrient and caustic feed systems. Soda ash was used to control pH, and a soluble fertilizer, in this case fish oil emulsion, was used as a nutrient. (Other types of soluble agricultural fertilizer can be used to supply nutrients.) The weight ratio of the nutrient comprised approximately 100 parts carbon:10 parts nitrogen:1 part phosphate. The fertilizer was added continuously to the influent contaminant stream by using a LMI model A771-152S chemical metering pump. The liquid level in the reactor was controlled by using two Dwyer model 603-A level transmitters set to maintain a reactor liquid volume of from 700 to 900 gallons.

Temperature was controlled by using a Ametek #20 Big Blue 1" heat exchanger and cooling water from the site.

Figure 7:
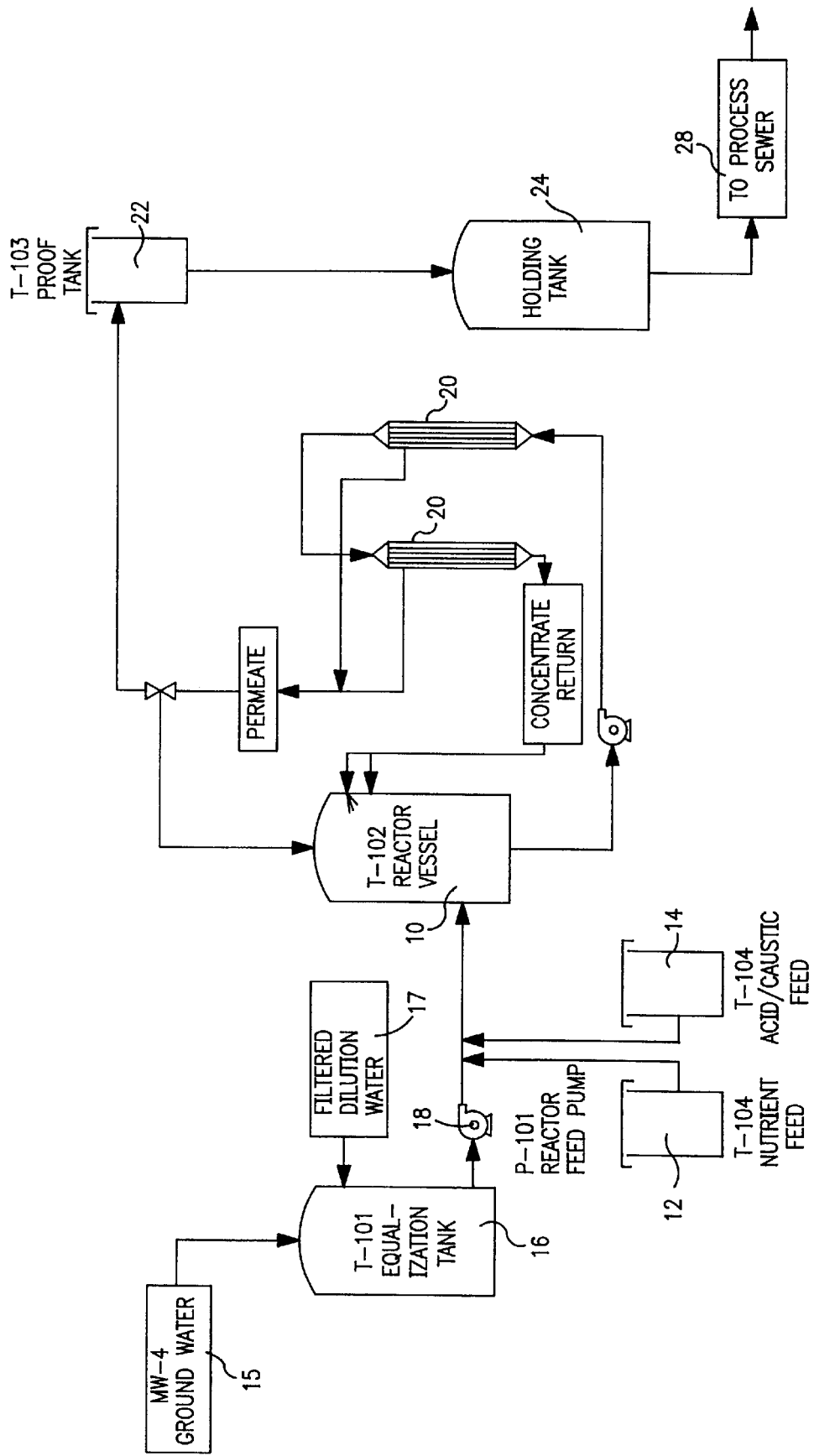
FIG. 7 is a schematic of a field-scaled membrane bioreactor system.

The pH was monitored and controlled by using a Rosemount model 1055APH pH analyzer/controller and a Rosemount model 385-2-8-54 pH sensor that measured pH in the reactor. Caustic was added to the influent feed line by using an LMI model A771-152S chemical metering pump. Effluent from the reactor was passed over dual ultrafiltration membranes (Rhone Poulenc model SC37/KO9; 17.22 ft$^2$ of membrane surface) connected in series, then into a proof tank and then a holding tank prior to discharge into the plant's sewer system. MTBE-contaminated groundwater (13,000 to 28,000 mg/L MTBE) was removed from a monitoring well on the site and placed into a 1000-gallon equilibration tank to create a feed concentration of 40 to 2400 mg/L MTBE. A schematic of the reactor system is shown in FIG. 7.

Operation of the reactor system was initiated by adding 225 gallons of water to the reactor and then adding concentrated BSM solution (see above) to the reactor to create a liquid concentration of 1×BSM. Twenty liters of frozen propane-grown ENV425 that had been grown in a laboratory fermentor in BSM medium with propane as a sole source of carbon and energy was frozen prior to shipment, then thawed and added directly to the water in the reactor. The ENV425 had an optical density at 550 nm of 20 in a spectronic 20 spectrophotometer prior to addition to the reactor. After addition to the reactor, the ENV425 was mixed well until dispersed. Then, 1.1 L of isopropanol were added while the reactor was mixing. The reactor was operated for 1.5 days until the culture became turbid. The reactor volume was then increased to 800 gallons, additional BSM was added to a final concentration of 1×BSM and an additional 3.8 L of isopropanol were added. The reactor was allowed to operate for an additional 2 days until the added isopropanol was consumed to increase biomass, prior to the addition of MTBE.

After cell density in the reactor had increased, MTBE-contaminated groundwater was added to the reactor to create a final concentration of 40 mg/L MTBE. Additional MTBE was added every 3 to 4 days, and the reactor was monitored for MTBE concentration, oxygen concentration (O&G), ammonia, total suspended solids (TSS), volatile suspended solids (VSS), pH, dissolved oxygen (DO), temperature, and oxygen uptake rate (OUR). This initial operation was termed the "batch phase" and was used to ensure equilibration of the reactor prior to initiating continuous feed operation. During the batch operation, the reactor contents were periodically passed over the ultrafiltration membranes to equilibrate the organisms to the sheer forces exhibited by the membrane system.

The continuous feed operation of the reactor was initiated by filling the equilibration tank with water and MTBE-contaminated groundwater to a final MTBE concentration of approximately 100 mg/L. The feed solution was then fed into the reactor at a rate of approximately 11 gallons/hr to create a hydraulic retention time in the reactor of approximately 3 days. Reactor effluent was passed over the ultrafiltration membranes and retenate, containing the propane-oxidizing bacteria, was returned to the reactor. Filtrate was passed to the proof tank, and a portion of the filtrate was pumped back into the reactor to maintain an appropriate liquid volume. This was done because the flux through the membrane (40 gal./day/ft$^2$ of membrane) was greater than the feed rate to the reactor. Some of the return liquid passed through a spray nozzle at the top of the reactor to control reactor foaming. Again, the reactor was monitored for MTBE concentration, oxygen concentration (O&G), ammonia, total suspended solids (TSS; also reported as "mixed liquor total suspended solids"; MLTSS), volatile suspended solids (VSS), pH, dissolved oxygen (DO), temperature, and oxygen uptake rate (OUR). Additionally, periodic samples of the reactor headspace were sampled to estimate MTBE stripping in the reactor.

During the continuous flow test, isopropanol was added to the equilibration tank, first in intermittent additions, then in a 1:1 ratio with the MTBE concentration. Isopropanol was used to rapidly increase biomass in the reactor and to maintain high levels of activity by the propane-oxidizing bacteria.

Results of batch and continuous reactor operation are shown, respectively, in Tables 3 and 4 below.

TABLE 3

Analytical Data-Batch Operations

| Batch No. | Date | MTBE mg/L | O&G mg/L | NH$_3$ mg/L | TSS mg/L | VSS mg/L | pH SU | DO mg/L | OUR mg/L/hr | Temp °C. |
|---|---|---|---|---|---|---|---|---|---|---|
| 1 | 12/4 | 40 | 10.3 | 0.03 | NA | NA | NA | NA | NA | NA |
|   | 12/6 | 15 | NA[a] | 224[b] | 400 | 357 | 7.45 | NA | NA | NA |
|   | 12/8 | 1.5 | NA | NA | NA | NA | NA | 5.5 | 18.4 | NA |
| 2 | 12/8 | 40 | 10.3 | NA | NA | NA | NA | 5.5 | 18.4 | NA |
|   | 12/13 | 2.5 | <5.4 | NA | 873 | 753 | 6.74 | 1.3 | 73.8 | NA |
| 3 | 12/13 | 40 | 10.3 | NA | NA | NA | 6.74 | 1.3 | 73.8 | NA |
|   | 12/16 | 0 2 | 12 | NA | 450 | 413 | 4.50 | BDL | NA | NA |
|   | 12/19 | BDL[c] | <5.4 | NA | 1410 | 1300 | NA | BDL | NA | NA |
| 4 | 12/19 | 40 | 10.3 | NA | NA | NA | NA | BDL | NA | NA |
|   | 12/22 | NA | 20.5 | 27.6 | NA | NA | 8.54 | 7.52 | 8 | NA |
| 5 | 12/22 | 76.7 | 20.5 | 27.6 | NA | NA | 8.54 | 7.52 | 8 | NA |
|   | 12/27 | 12 | <5.4 | 36 | 1600 | 1430 | 8.85 | 12.5 | NA | NA |
| 6 | 12/27 | 76.7 | 20.5 | 36 | 1600 | 1430 | 8.85 | 12.5 | NA | NA |
|   | 12/29 | 24 | <5.6 | NA | 1400 | 1200 | 8.63 | 18.8 | 48 | NA |
| 7 | 12/29 | 110 | 8.7 | NA | 1400 | 1200 | 8.63 | 18.8 | 48 | NA |
| 8 | 12/31[d] | 85.2 | 17.4 | 30 | NA | NA | 8.10 | 10.8 | 38.4 | 13 |
|   | 1/4 | 15 | <5.6 | 28.6 | 1400 | 1200 | 8.30 | 10.7 | 26 | 12 |
|   | 1/8 | 1.9 | <17 | 37 | 1360 | 1190 | 8.17 | 13.3 | 24 | 11 |
| 9 | 1/8 | 41 | 10.3 | 37 | 1360 | 1190 | 8.17 | 13.3 | 24 | 11 |
|   | 1/12 | 8.85 | <5.6 | 33.6 | 1470 | 1290 | 7.64 | 10.1 | 20 | 17 |
| 10 | 1/12 | 115 | 16.5 | 33.6 | 1470 | 1290 | 7.64 | 10.1 | 20 | 17 |
|   | 1/15 | 22 | <5.4 | 26 | 940 | 750 | 7.71 | 8.2 | 39.6 | 23 |
|   | 1/17 | 0.23 | NA | 21.8 | NA | NA | 7.82 | 6.2 | 54 | 32 |

[a]NA = Not analyzed
[b]Excess ammonia was added to the reactor tank.
[c]BDL = Below detection limit
[d]Additional 20 liters of contaminated ground water was added to reactor on 12/31.

TABLE 4

MTBE Loading vs. Removal Efficiencies - Continuous Operation

| Date | T-101 MTBE mg/l | T-103 MTBE mg/l | T-102 MLTSS mg/l | Mass of MLTSS (lb) | Loading (lb MTBE/lb TSS-day) | MTBE Removed | | (lb MTBE/ lb TSS-day) |
|---|---|---|---|---|---|---|---|---|
| | | | | | | Removed (lb/day) | (% Removed) | |
| 1/29 | 100 | 3.6 | 2280 | 15.2 | 0.008 | 0.12 | 96.4 | 0.008 |
| 2/2 | 250 | 5.2 | NA | NA | NA | 0.31 | 97.9 | NA |
| 2/7 | NS | 51 | 2740 | 18.3 | NA | NA | NA | NA |
| 2/9 | NS | 18 | 4400 | 29.4 | NA | NA | NA | NA |
| 2/12 | 240 | 20 | 2050 | 13.7 | 0.022 | 0.28 | 91.7 | 0.020 |
| 2/16 | 200 | 9.5 | 1760 | 11.7 | 0.022 | 0.24 | 95.3 | 0.021 |
| 2/19 | 280 | 11 | 1620 | 10.8 | 0.033 | 0.34 | 96.1 | 0.032 |
| 2/21 | NS | NS | 1280 | 8.5 | NA | NA | NA | NA |
| 2/26 | 410 | 1.6 | 1030 | 6.9 | 0.119 | 0.82 | 99.6 | 0.119 |
| 3/1 | 780 | 24 | 1300 | 8.7 | 0.180 | 1.51 | 96.9 | 0.174 |
| 3/4 | 680 | 24 | 1400 | 9.3 | 0.146 | 1.31 | 96.5 | 0.140 |
| 3/7 | 770 | 30 | 1620 | 10.8 | 0.142 | 1.48 | 96.1 | 0.137 |
| 3/11 | 2000 | 60 | 1910 | 12.8 | 0.314 | 3.88 | 97.0 | 0.304 |
| 3/14 | 1100 | 88 | 2430 | 16.2 | 0.136 | 2.02 | 92.0 | 0.125 |
| 3/18 | 1900 | 10 | 2300 | 15.4 | 0.247 | 3.78 | 99.5 | 0.246 |
| 3/21 | 1600 | 120 | 2110 | 14.1 | 0.227 | 2.96 | 92.5 | 0.210 |
| 3/25 | 1500 | 45 | 1860 | 12.4 | 0.241 | 2.91 | 97.0 | 0.234 |
| 3/28 | 2000 | 92 | 2390 | 16.0 | 0.250 | 3.82 | 95.4 | 0.239 |
| 4/1 | 2200 | 70 | 2490 | 16.6 | 0.264 | 4.26 | 96.8 | 0.256 |
| 4/4 | 2400 | 49 | 2650 | 17.7 | 0.271 | 4.70 | 98.0 | 0.266 |
| 4/8 | 1700 | 91 | 3170 | 21.2 | 0.161 | 3.22 | 94.6 | 0.152 |
| Avg. | 1083 | 39 | 2085 | 13.9 | 0.164 | 2.04 | 96.2 | 0.158 |

T-101 = Equalization Tank;
T-102 = Bioreactor;
T-103 = Effluent Proof Tank

After an initial start-up period of only 4 days, the reactor operated successfully for approximately 4 months. Greater than 90% MTBE removal was achieved throughout the demonstration, despite great fluctuations in pH and temperature, and an increasing MTBE concentration from 40 mg/L to >2000 mg/L. During continuous feeding, mixed liquor suspended solids increased to >3000 mg/L. Loss of MTBE caused by stripping/volatilization averaged only 4.5% during the demonstration, as shown the measurements presented in Table 5 below.

TABLE 5

Volatilization Losses

| | 3/7 | 3/25 | 4/1 | 4/8 | 4/15 | Averages |
|---|---|---|---|---|---|---|
| Influent MTBE mg/L | 770 | 1500 | 2200 | 1700 | 1700 | 1574 |
| Influent Flow gpm | 0.177 | 0.167 | 0.172 | 0.184 | 0.186 | 0.177 |
| Influent MTBE lbs/day | 1.64 | 3.01 | 4.54 | 3.75 | 3.79 | 3.35 |
| Headspace MTBE ppmv | 190 | 25 | 300 | 210 | 78 | 161 |
| Air Flow scfh | 160 | 200 | 200 | 160 | 200 | 184 |
| MTBE volatilized lbs/day | 0.157 | 0.026 | 0.311 | 0.174 | 0.081 | 0.150 |
| MTBE Loss % | 9.6 | 0.9 | 6.8 | 4.6 | 2.1 | 4.5 |

Example 12
In Situ Remediation of Gasoline Oxygenates

In situ remediation of gasoline oxygenates will be performed by adding co-substrates (propane or butane) and oxygen (as air or pure $O_2$) directly to the contaminated media. It is believed that organisms capable of oxidizing propane may have the ability to oxidize butane. Accordingly, it may be desirable in certain situations to utilize butane at a given site. The gas injection will stimulate the growth and degradative activity of naturally-occurring propane or butane-degrading organisms, thereby allowing them to fortuitously degrade the gasoline oxygenates.

Gasses will be added to the subsurface either by injection/vapor extraction (vadose zone) or by in situ gas sparging (saturated zone) as previously described (Marley, M. C., E. X. Droste, H. H. Hopkins, and C. J. Bruell, "Use Air Sparging to Remediate," *Environ. Engineer. World*, 6–14 (March–April 1996). When these techniques are used to stimulate the growth and activity of natural pollutant degrading microorganisms, they are referred to as "bioventing" and "biosparging", respectively, and "biostimulation" collectively. The use of gas (methane) injection to remediate aquifers contaminated with trichloroethylene has been demonstrated (Semprini, L. and P. L. McCarty, "Comparison between model simulations and field results from in situ biorestoration of chlorinated aliphatics: Part 1, biostimulation of methanotropic bacteria," *Ground Water*, 29:365–374 (1991); Roberts, P. V., G. D. Hopkins, D. M. Mackay, and L. Semprini, "A field evaluation of in situ biodegradation of chlorinated ethanes: Part I, methodology and field site characterization," *Ground Water*, 28:591–604 (1990); and Brockman, F. J., W. Payne, D. J. Workman, A. Soong, S. Manley, and T. C. Hazen, "Effect of gaseous nitrogen and phosphorous injection on in situ bioremediation of a trichloroethylene-contaminated site," *J. Haz. Material*, 41:287–298 (1995)).

To perform in situ biostimulation for destruction of gasoline oxygenates, air, oxygen, propane, and/or butane (co-substrate) will be injected into the subsurface by inserting injection wells into either the vadose or saturated zones. Vapor extraction wells will be inserted into the vadose zone to capture the gasses and direct the flow of gas within the subsurface. Methods for designing and implementing sparging and vapor extraction systems have been described in detail (Marley, M. D., D. J. Hazebrook, and M. T. Walsh, "The application of in situ air sparging as an innovative soils and groundwater remediation technology," *Groundwater Monitoring Review*, 2:137–145 (1992)). Co-substrate and air/oxygen will be injected simultaneously in a 1:100 mixture of propane in air. The system will be operated by injecting the gas mixture for 10 min. every half hour at a rate of 10 ft$^3$/min. Alternately, the substrates, air and propane, will be added independently by first injecting propane for 4 hours at a rate of 1 to 10 ft$^3$/min., then injecting air at the same rate for 4 hours. If additional nutrients are needed to obtain higher numbers of propane oxidizing bacteria, the gaseous nutrients ammonia and triethylphosphate will be injected through the in situ injection system. (See Brockman, F. J. et al. supra.)

The concentration of gasoline oxygenates in the subsurface will be monitored by analyzing vapors recovered by the vapor extraction system, and/or by monitoring liquid-phase concentrations of oxygenates in the groundwater. Vapors will be collected in Tetlar bags and analyzed by gas chromatography, and aqueous samples will be collected from monitoring wells and similarly analyzed by gas chromatography.

To confirm the increase in numbers of indigenous propane oxidizing bacteria, samples of the contaminated media will be diluted and spread onto the surface of BSM agar plates. The plates will then be incubated in sealed jars containing an atmosphere of propane and air (1:100 v/v). Colonies of propane oxidizing bacteria will be enumerated by counting the colonies that form on the plates. The increase in microbial numbers will be determined by comparing the number of organisms present before and after injection of the substrates.

In the event that the numbers of naturally-occurring propane oxidizing bacteria are low and limit the performance of the system, propane oxidizing bacteria will be added to the contaminated media prior to propane and air injection. Propane oxidizing bacteria (either *M. vaccae* JOB5, ENV420, ENV421, ENV425, indigenous propane oxidizers, or a combination of these) will be grown in laboratory or on-site fermentors and injected into wells inserted into the contaminated media. Organisms will be added to obtain a final cell concentration of 1×10$^4$ to 1×10$^8$ cells/ml (gm) of contaminated media. Propane and air injection will then be performed as described above to stimulate the growth and degradative activity of the added organisms. The survival and growth of the added organisms will be performed by plating as described above, and degradation of gasoline oxygenates will be performed by gas chromatographic analysis of vapor, soil, and water samples as previously described.

Example 13
Degradation of Tert-amyl Methylether (TAME) by Propane-Oxidizing Bacteria A number of experiments were conducted to measure the ability of propane-oxidizing bacteria to degrade tert-amyl methyl ether (TAME) after growth on different carbon sources. Cells of *M. vaccae* JOB5, ENV420, ENV421, ENV425 and a mixed bioreactor culture of propane-oxidizing bacteria from a laboratory reactor (termed "TXR") were grown in BSM medium with either propane, acetone, isopropanol, 1-propanol, or ethanol as the sole source of carbon and energy, collected by centrifugation, washed with BSM, and suspended in BSM to an optical density at 550 nm of 2.0. Five milliliters of the cell suspensions, in triplicate, were added to 15 mL serum vials, and the vials were sealed with Teflon-lined septa and crimp tops. Vials containing BSM but no cells, and vials containing HgCl$_2$-poisoned *M. vaccae* JOB5 ("killed") served as controls. Tert-amyl methyl ether was injected through the septa to create a final liquid concentration of 7.8 mg/L. The vials were then incubated at room temperature for 24 hours and the culture fluid was analyzed by gas chromatography as described for MTBE analysis. Data represent the concentration of TAME remaining (in ppm) after incubation with the cell cultures.

The results of these studies are presented in Table 6. The results demonstrate the ability to completely degrade TAME with propane-oxidizing bacteria grown with propane as a source of carbon. Similarly, for *M. vaccae* JOB5 and ENV421, other growth on other growth substrates also resulted in complete degradation of TAME.

TABLE 6

Degradation of TAME (tert amyl methyl ether) for 24 Hours by Different Cultures after Growth on Select Media

| Culture | Media | TAME, ppm Remaining after 24 hr incubation | | | |
| --- | --- | --- | --- | --- | --- |
| | | Sample 1 | Sample 2 | Sample 3 | Average |
| Control (BSM) | | 7.5 | 8.3 | 7.6 | 7.8* |
| *M. vaccae*-kill | Acetone | 7.2 | 6.5 | 5.4 | 6.2 |
| *M. vaccae* | Acetone | 0 | 0 | 0 | 0 |
| *M. vaccae* | Propionic Acid | 3.2 | 3.1 | 3.2 | 3.2 |
| *M. vaccae* | Ethanol | 0 | 0 | 0 | 0 |
| *M. vaccae* | Propane | 0 | 0 | 0 | 0 |
| *M. vaccae* | 1-Propanol | 0 | 0 | 0 | 0 |
| 420 | Ethanol | 4.6 | 4.8 | 4.6 | 4.7 |
| 420 | 1-Propanol | 7.3 | 7.7 | 7.7 | 7.6 |
| 420 | Propane | 0 | 0 | 0 | 0 |
| 421 | Ethanol | 4.3 | 4.0 | 3.9 | 4.1 |
| 421 | 1-Propanol | 0 | 0 | 0 | 0 |
| 421 | Propane | 0 | 0 | 0 | 0 |
| 425 | Acetone | 0 | 0 | 2.8 | 0.9 |
| 425 | Isopropanol | 4.6 | 4.7 | 5.0 | 4.8 |
| 425 | Propionic acid | 0 | 0 | 0 | 0 |
| 425 | Ethanol | 2.7 | 2.6 | 0 | 1.8 |
| 425 | Propane | 0 | 0 | 0 | 0 |
| TXR | Acetone | 3.8 | 3.8 | 2.8 | 3.5 |
| TXR | Propionic Acid | 4.0 | 4.1 | 4.1 | 4.1 |
| TXR | Ethanol | 4.5 | 4.5 | 4.7 | 4.6 |
| TXR | Isopropanol | 3.7 | 3.9 | 3.7 | 3.8 |
| TXR | Propane | 0 | 0 | 0 | 0 |

*—Starting Concentration

Example 14
Degradation of Tetrahydrofuran

To test the ability of propane oxidizing bacteria to degrade other environmentally-significant ether pollutants, ENV425 and a mixed culture of propane oxidizing bacteria from a laboratory bioreactor were incubated with tetrahydrofuran, and the degradation of tetrahydrofuran was measured after 48 hours. Cells of ENV425 and a mixed bioreactor culture of propane oxidizing bacteria (termed "TXR") were grown in BSM medium with propane as the sole source of carbon and energy, collected by centrifugation, washed with BSM, and suspended in BSM to an optical density at 550 nm of 2.0. Five ml of the cell suspensions were added to 15 mL serum vials, and the vials were sealed with Teflon-lined septa and crimp tops. Vials containing BSM but no cells served as controls. Tetrahydrofuran was injected through the septa to create a final liquid concentration of 40 mg/L. The vials were then incubated at room temperature for 48 hours and analyzed by gas chromatography of subsamples of the vial headspace gas. Gas chromatography was performed as described for MTBE analysis.

Results of the tetrahydrofuran degradation study demonstrated that 100% of the tetrahydrofuran was degraded in samples containing either ENV425 or the mixed culture of propane oxidizing bacteria, whereas no tetrahydrofuran was degraded in cell-free control samples. No other volatile degradation products were identified in samples containing ENV425 or the mixed culture of propane oxidizing bacteria.

We claim:

1. A method for degrading an ether comprising contacting said ether with a propane-oxidizing bacteria.

2. The method of claim 1 wherein said ether is a methyl tert-butyl ether.

3. The method of claim 1 wherein said ether is selected from the group consisting of ethyl tert-butyl ether, TAME, tetrahydrofuran, and diisopropyl ether.

4. The method of claim 1 including the use of a co-substrate to support degradation of said ether by said bacteria.

5. The method of claim 1 wherein said ether is present in water.

6. The method of claim 5 wherein said ether is methyl tert-butyl ether.

7. The method of claim 1 wherein said ether is present in soil.

8. The method of claim 7 wherein said ether is methyl tert-butyl ether.

9. The method of claim 1 wherein the bacteria consists essentially of a propane-oxidizing bacteria.

10. The method of claim 9 wherein said propane-oxidizing bacteria is selected from the group consisting of *Mycobacterium vaccae* JOB5, ATCC 29678; Strain ENV420; Strain ENV421; and Strain ENV425.

11. The method of claim 9 wherein the ether is MTBE.

12. The method of claim 11 wherein said propane-oxidizing bacteria is selected from the group consisting of *Mycobacterium vaccae* JOB5, ATCC 29678; Strain ENV420; Strain ENV421; and Strain ENV425.

13. The method according to claim 1 wherein said ether is contacted with said bacteria within a bioreactor.

14. The method of claim 13 including the use of a co-substrate to support degradation of said ether by said bacteria.

15. The method of claim 14 wherein said co-substrate is acetone, ethanol or butane.

16. The method of claim 13 wherein said bioreactor is a suspended growth bioreactor.

17. The method of claim 16 wherein said bioreactor is a membrane bioreactor.

18. The method according to claim 1 wherein said ether is contacted with said bacteria in situ.

19. The method of claim 18 wherein said ether is present in groundwater.

20. The method of claim 18 wherein said ether is present in soil or sludge.

21. The method according to claim 1 wherein said ether is tetrahydrofuran.

22. A method for degrading tert-butyl alcohol comprising contacting said alcohol with a propane-oxidizing bacteria.

* * * * *